US007002682B2

(12) United States Patent
Girvin et al.

(10) Patent No.: US 7,002,682 B2
(45) Date of Patent: Feb. 21, 2006

(54) METHOD AND APPARATUS FOR OPERATING A LASER IN AN EXTINCTION-TYPE OPTICAL PARTICLE DETECTOR

(75) Inventors: Kenneth L. Girvin, Grants Pass, OR (US); Adam J. Reed, Ashland, OR (US)

(73) Assignee: Hach Ultra Analytics, Inc., Grants Pass, OR (US)

(*) Notice: Subject to any disclaimer, the term of this patent is extended or adjusted under 35 U.S.C. 154(b) by 77 days.

(21) Appl. No.: 10/778,968

(22) Filed: Feb. 13, 2004

(65) Prior Publication Data

US 2005/0179896 A1 Aug. 18, 2005

(51) Int. Cl.
*G01N 15/02* (2006.01)
(52) U.S. Cl. ..................... 356/335; 356/338
(58) Field of Classification Search ............... 356/335, 356/336, 337, 338, 342, 343, 447
See application file for complete search history.

(56) References Cited

U.S. PATENT DOCUMENTS

| 5,475,235 A | 12/1995 | Phillips et al. ............... 250/574 |
| 6,784,981 B1 * | 8/2004 | Roche et al. .................. 356/39 |

FOREIGN PATENT DOCUMENTS

JP  09-178645  7/1997

OTHER PUBLICATIONS

Akira Arimoto, et al., "Optimum Conditions for the High Frequency Noise Reduction Method in Optical Videodisc Players," published in *Applied Optics*, vol. 25, No. 9, May 1, 1986.
Masahiro Ojima, et al., "Diode Laser Noise at Video Frequencies in Optical Videodisc Players", published in *Applied Optics*, vol. 25, No. 9, May 1, 1986.
K. Petermann, book entitled *Laser Diode Modulation and Noise*, Copyright 1988 by Kluwer Academic Publishers, Chapter 4, pp. 100 to 105.

* cited by examiner

*Primary Examiner*—Gregory J. Toatley, Jr.
*Assistant Examiner*—Roy M. Punnoose
(74) *Attorney, Agent, or Firm*—Stoel Rives LLP

(57) ABSTRACT

A light-extinction-type optical particle detection system comprises a laser producing a beam in response to a drive current amplitude reaching a lasing threshold, a view volume, and a light-extinction detector. The beam is characterized by mode-hopping noise energy produced by spurious switching of laser operating modes. The system comprises a signal generator producing the drive current such that its amplitude transitions across the threshold by a selected amount and at a selected frequency to cause the beam to operate simultaneously in multiple modes. The selected amount and frequency cooperate to spread the mode-hopping noise energy over a spectral range established by the number of modes, such that the detector does not appreciably respond to the mode-hopping noise energy.

26 Claims, 5 Drawing Sheets

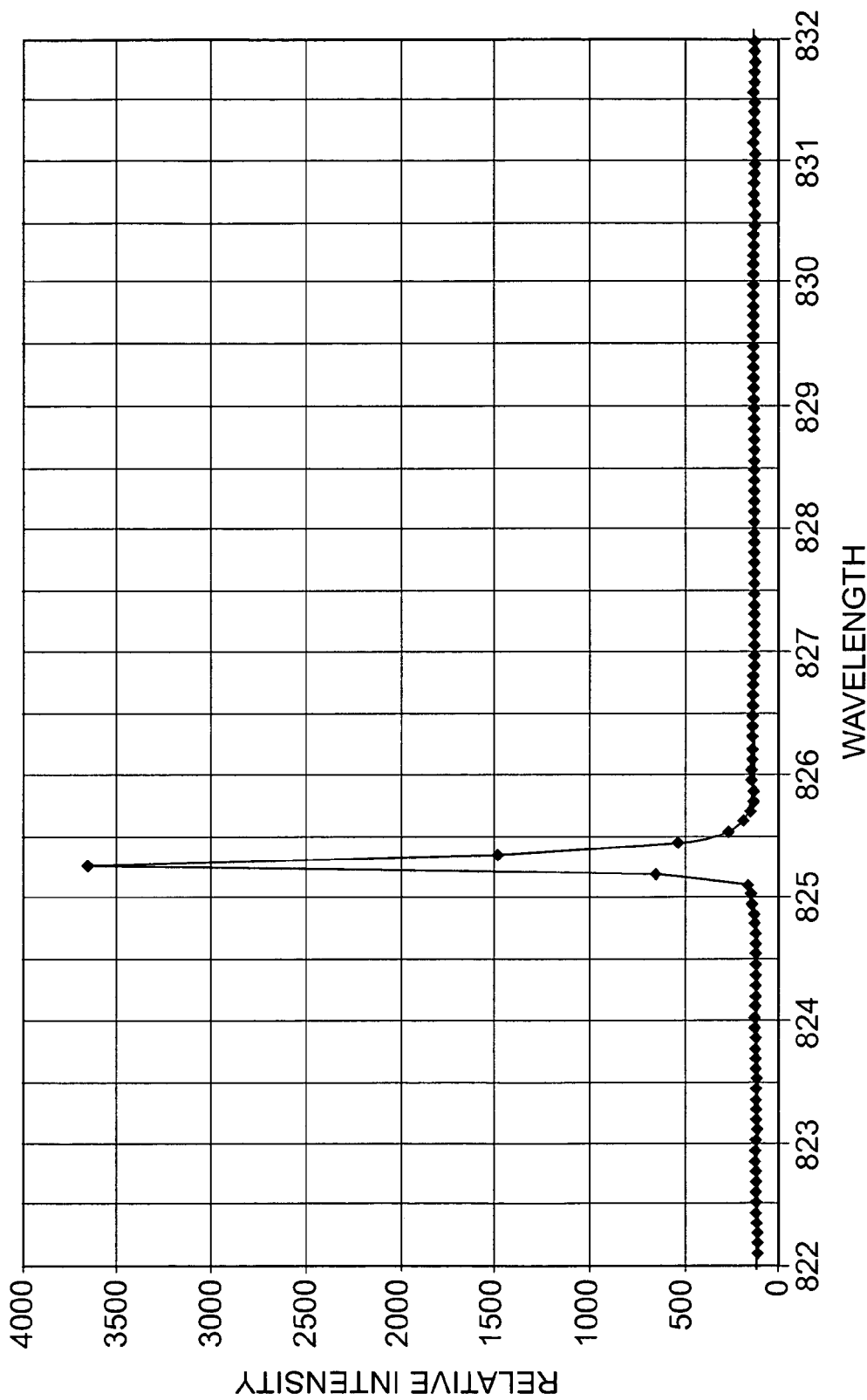
FIG. 3A  LASER SPECTRUM -- WITHOUT MODULATION

METHOD AND APPARATUS FOR OPERATING A LASER IN AN EXTINCTION-TYPE OPTICAL PARTICLE DETECTOR

TECHNICAL FIELD

This invention relates generally to optical particle detection and more specifically to operation of a laser in an optical particle detection system.

BACKGROUND OF THE INVENTION

Optical particle detection systems are useful for applications such as contamination control, which is critically important in the manufacturing processes of several industries. These industries may require cleanrooms or clean zones with active air filtration, as well as a supply of clean raw materials such as process gases, deionized water, chemicals, and substrates. For example, in the pharmaceutical industry, the Food and Drug Administration requires particulate monitoring because of the correlation between detected particles in an aseptic environment and viable particles that contaminate the product produced. As another example, semiconductor fabrication companies require particulate monitoring as an active part of quality control.

Optical particle detection systems utilize illumination to determine the presence, size, number and/or concentration of particles in a volume. The particles are typically suspended in a fluid, which may flow through the volume that is illuminated and viewed by the detection system. The basic components of such a system are a laser illumination source; a view volume in which the particles to be detected may reside and into which the illumination is directed; and one or more sensors, which are typically photodetectors, that can detect optical disturbances of the illumination caused by the particles in the view volume.

The illumination source in an optical particle detection system is typically a semiconductor diode laser. The source ideally is stable, quiet, and has lone life. There are two basic types of diode lasers used in particle detectors: gain-guided and index-guided. Gain-guided lasers are typically quiet enough for a particle detection system because at any given time they have many longitudinal modes running, which allows for an averaging effect over all the modes. When one mode turns off and another turns on, as for instance when the temperature or drive current changes, the average light is relatively constant. Suitable gain-guided lasers, however, are short-lived, having a typical useful life of approximately sixteen to eighteen months of continuous operation in the absence of effective countermeasures.

Index-guided lasers, on the other hand, typically have a much longer useful life, with a mean-time-to-failure as long as eight years. Index-guided lasers, however, suffer from a problem associated with mode hopping. Unlike a gain-guided laser, an index-guided laser typically operates in one dominant longitudinal mode of lasing. When used in continuous-wave mode, index-guided lasers often switch modes or mode-hop as the temperature or other external conditions change, and they are therefore not sufficiently stable for use in a particle detection system. The mode hops can create noise levels higher than the relative intensity noise (RIN) in the laser beam, thereby causing false counts. Furthermore, as a laser ages or when the operating temperature increases, more drive current is required to maintain constant power. While that fluctuation can be compensated for with the use of an automatic power control circuit, raising the drive current increases the junction temperature, which consequently increases the laser beam's wavelength. Unfortunately, the wavelength shift is not gradual; the wavelength will abruptly change from one mode to another at specific operating conditions, and frequency instabilities and excess noise can occur at those mode-hopping points. To combat those ill effects, one class of known prior art uses active temperature compensation and a constant laser drive current to stabilize the laser beam's wavelength in areas between mode-hopping points.

Mode hopping therefore directly imposes a serious limitation on the usefulness of an index-guided laser and, by necessitating the use of shorter-lived gain-guided lasers, indirectly imposes a serious limitation on the useful life of a laser in an optical particle detection system. The consequent frequent replacement of lasers in such systems represents a significant cost and burden to the users of such systems.

To make matters worse, laser mode hopping is especially problematic when the sensor is of the light-extinction type. Sensors in optical particle detection systems come in two varieties: light-scattering and light-extinction. Light-scattering sensors, as the name implies, detect scattered light from a particle when it passes through the laser beam. A standard particle detection system operating according to the light-scattering principle passes a fluid sample stream containing the particles through an elongated flattened nozzle such that the sample stream exiting the nozzle intersects a laser beam in a view volume. Scattered light from particles in the view volume is collected with optics and processed to determine such things as particle counts or sizing information. On the other hand, light-extinction sensors detect the amount of loss in a laser beam when the particle passes through it. Unlike light-scattering type sensors, which can be designed to minimize the amount of detectable background light and therefore minimize the amount of detectable mode-hopping noise, light-extinction type sensors are typically illuminated directly by the laser beam, so any small change in the laser light, such as mode-hopping noise, is very likely to be detected as false counts. That is because a typical sensor is sensitive to light level changes on the order of nanowatts, such as when a particle passes through the laser beam. Thus, any instabilities or RIN in the laser beam may be detected as false particle counts, as an increase in the RIN from the laser can cause the sensor's output signal to exceed the shot noise generated by background light impingent on the sensor.

In contexts other than particle detection systems, it has been known to decrease mode-hopping noise by modulating an index-guided laser, so as to cause multi-mode lasing. That technique has been applied successfully in videodisc players, for example. Although Japanese Patent Application No. 09-1786645 describes the same technique used in a light-scattering type optical particle detection system, to our knowledge, no one has successfully utilized that technique in an optical particle detection system of the light-extinction type.

SUMMARY OF THE INVENTION

In one respect, the invention is a method for use in an optical particle detection system of a light-extinction type that includes a view volume through which a laser beam propagates and a stream of target particles immersed in a carrier fluid flows. The laser beam strikes the target particles and thereby affects an amount of the laser beam that is incident on a light-sensitive detector positioned in optical communication with the view volume. The light-sensitive detector produces, in response to the incident laser beam, a detection signal corresponding to a number and/or size of target particles in the stream. The laser beam propagates from a laser source in response to a drive current amplitude that reaches a lasing threshold. The laser beam is characterized by noise energy that is produced by spurious switching of laser operating modes. The method controls the laser source to emit a laser beam in which the noise energy is suppressed to a level that does not appreciably affect the fidelity of the signal produced by the light-sensitive detector. The method comprises a step of modulating the drive current amplitude to transition across the lasing threshold by a selected amount and at a selected frequency to purposefully cause multiple simultaneous laser operating modes. The selected amount and frequency of modulation of the drive current amplitude cooperate to cause the spurious mode switching to occur among a number of laser operating modes sufficient to spread the noise energy produced over a spectral range established by the number of laser operating modes. The spreading of the noise energy causes the noise energy to maintain a level to which the light-sensitive detector does not appreciably respond in the production of the detection signal.

In another respect, the invention is a light extinction-type optical particle detection system. The system comprises a laser source that produces a laser beam. The laser beam propagates from the laser source in response to a drive current having an amplitude that reaches a lasing threshold. The laser beam is characterized by mode-hopping noise energy that is produced by spurious switching of laser operating modes. The system also comprises a view volume through which the laser beam propagates and a stream of target particles immersed in a carrier fluid flows. The system also comprises a light-extinction type detector positioned on a side of the view volume opposite of the laser source. The laser beam strikes the target particles and thereby affects an amount of the laser beam that is incident on the detector, which produces, in response to the incident laser beam, a detection signal corresponding to the number of target particles in the view volume. The system also comprises a signal generator that produces the drive current such that the drive current amplitude transitions across the lasing threshold by a selected amount and at a selected frequency to purposefully cause the laser beam to operate simultaneously in multiple lasing modes. The selected amount and frequency cooperate to spread the mode-hopping noise energy over a spectral range established by the number of simultaneously operating lasing modes, such that the detector does not appreciably respond to the mode-hopping noise energy when producing the detection signal.

In yet another respect, the invention is an apparatus. The apparatus comprises a view volume through which a laser beam propagates and a stream of target particles immersed in a carrier fluid flows. The apparatus also comprises a means for detecting light, positioned in optical communication with the view volume. The apparatus also comprises a means for generating a laser beam striking the target particles and thereby affecting an amount of the laser beam that is incident on the means for detecting light. The laser beam is characterized by noise energy that is produced by spurious switching of laser operating modes. The apparatus also comprises a means for producing, in response to the incident laser beam, a detection signal corresponding to a number of target particles in the stream; and a means for spreading the noise energy over a spectral range, whereby the noise energy is maintained at a level to which the means for producing does not appreciably respond in the production of the detection signal.

Additional details concerning the construction and operation of particular embodiments of the invention are set forth in the following sections. As one skilled in the art will appreciate, certain embodiments of the invention are capable of achieving certain advantages over the known prior art, including some or all of the following: (1) mode hopping can truly and demonstrably be decreased in an optical particle detection system; (2) the reduction in mode-hopping noise can be significant enough to enable utilization of light-extinction sensors; and (3) the useful life of a laser in an optical particle detector can be significantly increased, thereby reducing downtime and the significant cost of replacing lasers. Those skilled in the art will appreciate these and other advantages and benefits of various embodiments of the invention upon reading the following detailed description of preferred embodiments with reference to the below-listed drawings.

BRIEF DESCRIPTION OF THE DRAWINGS

FIGS. 3A and 3B are wavelength-domain plots of the spectrum of a laser beam without and with the system of FIG. 1, respectively.

DETAILED DESCRIPTION OF PREFERRED EMBODIMENTS

Figure 1:
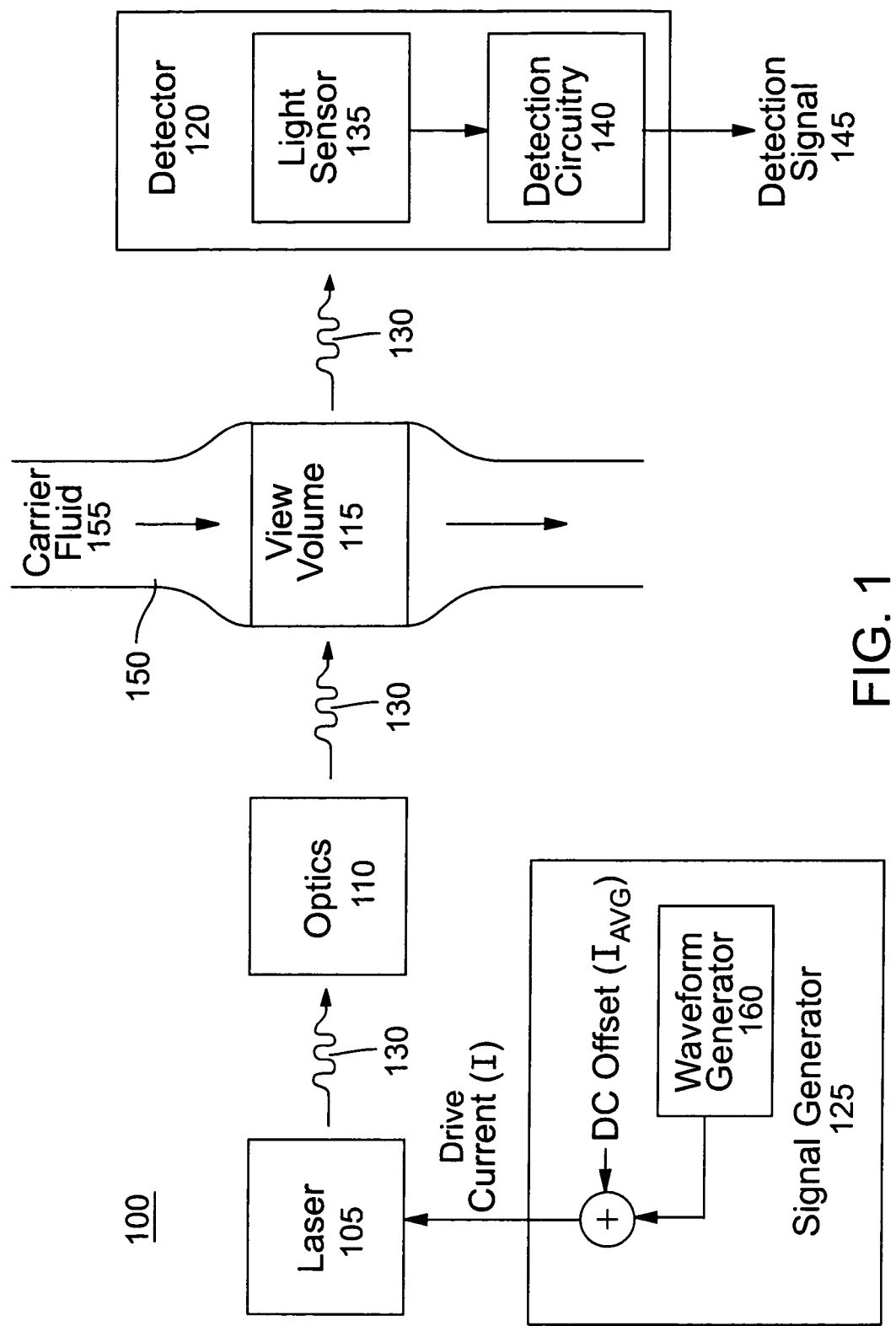
FIG. 1 is a block diagram of an optical particle detection system, according to one embodiment.

FIG. 1 is a block diagram of an optical particle detection system 100. The system 100 comprises a laser 105, optics 110, a view volume 115, a detector 120, and a signal generator 125. The system 100 generally operates as follows: In response to a drive current I generated by the signal generator 125, the laser 105 produces a laser beam 130, which is directed at the optics 110. The optics 110 focuses the laser beam 130 through the view volume 115 and onto the detector 120. The detector 120 comprises a light sensor 135 and detection circuitry 140. When a target particle is present in the view volume 115, that particle blocks at least a portion of the laser beam 130, thus decreasing the amount of optical energy incident upon the light sensor 135. By monitoring the light energy measured by the light sensor 135, counting how many times it temporarily decreases, and measuring the magnitude of those decreases, the detection circuitry 140 can determine the number and approximate size of the particles that pass through the view volume 115. A detection signal 145, which is the output of the detector 125, conveys the count and/or size information for the detected particles. Each component of the system 100 will next be described in greater detail.

The laser 105 is preferably a diode laser. The laser 105 produces the laser beam 130 when the drive current I meets certain conditions. More specifically, the laser 105 is characterized by a drive current threshold, and the drive current I must be near to or exceed that threshold in order for the laser 105 to begin lasing and thereby produce the laser beam 130. The transition from a non-lasing state to a lasing state is not necessarily a sharp one; hence, the threshold by its very nature may be approximate, in which case it can be sufficient to induce lasing if the amplitude of drive current I is merely close to the threshold. To be more assured that lasing will result, the amplitude of the drive current I should exceed the threshold by some margin.

If the drive current I has a constant amplitude of sufficient level, then the laser beam 130 will be a continuous-wave laser beam. If the laser 105 is an index-guided laser, then it will have a dominant mode, i.e., a wavelength or frequency at which all or most of the light energy in the laser beam 130 is concentrated. Unfortunately, under those conditions, the laser 105 can unpredictably and abruptly mode hop, i.e., change to a new dominant mode. A mode hop can, and usually does, cause a perturbation in the power of the laser beam 105 sufficient to be detected by the detector 120 and mistaken as a particle. In other words, mode hopping can cause false detections. By varying the amplitude of the drive current I, as explained in more detail below, the signal generator 120 aims to partially or completely eliminate mode hopping that can cause false detections.

The laser 105 is also characterized by a time parameter indicative of when mode hopping occurs relative to the onset of lasing. Under one theory, the time parameter is simply a time before which mode hopping will not likely occur. If that time parameter is denoted T, then the laser 105 will not likely mode hop within T time units (e.g., seconds or milliseconds) after lasing begins. Under another theory, the time parameter T is a measure of a settling time for the laser 105, such that the laser 105 does not settle into a single dominant mode of lasing until T time units after lasing begins. Until that time, under this theory, the laser 105 is believed to exhibit multiple lasing modes. More will be said about the drive current I and the time parameter T below in relation to the signal generator 125 and in relation to FIG. 2.

The optics 110 can comprise one or more optical elements, such as a collimator lens, a cylindrical lens, and two cell windows. The optics 110 preferably directs and focuses the laser beam 130 onto the view volume 115 and the light sensor 135 on the opposite side of the view volume 115. As one of skill in the art will appreciate, the optics 110 may not be necessary in some arrangements of the system 100.

It is possible that an optical element may cause a backward reflection of some portion of the laser beam 130 toward the laser 105. Such a reflection can disturb the standing wave oscillations in a cavity of the laser 105 and thereby cause noise in the system 100. For example, interferometric noise is caused by the conversion of laser phase noise into intensity noise by multiple reflections along the optical path of the laser beam 130. In some cases, a strong back reflection can cause certain lasers to become completely unusable. Back reflection can also generate nonlinearities (also referred to as "kinks") in the response of the laser 105. Those degradations cannot be tolerated in some systems. To alleviate troublesome back reflection, one or more optical elements in the optics 110 are preferably tilted at angles on the order of a few degrees or just large enough to prevent the laser beam 130 from reflecting back into the laser 105. Such tilting, though slight, significantly reduces back reflection noise and associated problems, thereby further increasing performance of the system 100 in addition to performance gains resulting from variation of the drive current I, as described below.

The view volume 115 is preferably a section of a flow path 150, through which a carrier fluid 155 flows. Suspended in the carrier fluid 155 are the particles of interest, which the system 100 is designed to detect, count, and/or size. The carrier fluid 155 is preferably a liquid. The flow path 150 may be formed by a nozzle or defined by a pipe or other conduit. The flow path 150 may be turbulent or laminar. As one skilled in the art will surely realize, FIG. 1 and in particular the flow path 150 and the view volume 115 are not drawn to scale or otherwise meant to accurately depict relative sizing or appearance of the physical components that constitute the system 100. Instead, the drawings are meant to illustrate the principles by which the system 100 operates.

The detector 120 is a light-extinction type detector located on a side of the view volume 115 opposite of the side into which the laser beam 130 enters the view volume 115. The detector 120 comprises the light sensor 135 and the detection circuitry 140. The sensor 135 is preferably a photodiode, which generates an electrical signal, the power of which is related to the amount of light energy incident upon the face of the sensor 135. The detection circuitry 140 receives the output of the sensor 135, preferably filters the output to remove unwanted glitches in the output, detects when the output changes (e.g., decreases in magnitude) in a way indicative of a target particle blocking the laser beam 130 in the view volume 115, preferably measures parameters of the output signal indicative of the size of the target particle (e.g., the extent of a decrease in magnitude), and preferably counts those changes. In other words, the detection signal 145 contains pulses, each of which represents one particle, and the amplitude of each pulse is directly proportional to the size of the particle.

While the output of the detection circuitry 120 is denoted as the detection signal 145, it should be apparent to those skilled in the art that the output of the sensor 135 is also a "detection signal," as it itself contains the relevant information concerning the presence, number, and/or size of the detected particles. In fact, in some cases, the detection circuitry 140 may be optional, being that it merely extracts from the output of the sensor 135 the particle count and/or size information and assembles that information into a form that may be more convenient for subsequent display, processing, storage, or transmission.

The detector 120 is characterized by a frequency response, which has an upper limit. That upper limit defines an effective detection rate. Put simply, the detector 120 is incapable of responding to variations in the laser beam 130 occurring faster than the effective detection rate. That limitation may be attributable to, for example, the frequency response of the sensor 135, the detection circuitry 140, or both. The system 100, and in particular the signal generator 125, is preferably designed to exploit that limitation, as explained more fully below.

Finally in regard to the detector 120, one should note that, although the detector 120 is just one component of the system 100, as labeled in FIG. 1, one may also refer to the overall detection system 100 as a "detector."

The signal generator 125 generates the drive current I so as to have a time-varying amplitude. Preferably, the drive current I is formed as the sum of a constant DC (direct current) offset component $I_{AVG}$ and a time-varying component, which is preferably generated by a waveform generator 160. The time-varying component is preferably periodic and may be of any waveform shape, such as, for example, sinusoidal, square, or sawtooth, or triangular. The waveform may have any arbitrary duty cycle, although 50% is preferred.

In the parlance of the laser art, the time variations in the amplitude of the drive current I "modulate" the laser beam 130. When the drive current I is a periodic signal, the frequency of the signal is the frequency of modulation ($f_{MOD}$). Moreover, the magnitude of the waveform variations translates to a depth of modulation. Those concepts and their significance are explained in more detail below with reference to FIG. 2.

The time variations in the amplitude of the drive current I are also understood to spread the spectrum of the laser beam 130. More specifically, the time variations cause the laser 105 to operate in a number of lasing modes simultaneously. As used herein, the notion of simultaneity of multiple lasing modes encompasses not only the case of actual, true simultaneity, but also the case of approximate simultaneity. An example of the latter case is when the laser beam 130 is in only one mode at any given time, but it changes modes more rapidly than the maximum frequency response of the detector 120, such that the detector 120 effectively sees multiple simultaneous lasing modes in the beam 130. Spreading of the spectrum of the laser beam 130 has been shown to significantly decrease the adverse effects of mode hopping. This is believed to be due to the fact that when the energy of the laser beam 130 is distributed among several modes, a hop of any one or a small number of modes to a new mode(s) is not so significant as to register as a false detection.

From another perspective, it is believed that variations in the amplitude of the drive current I, under the proper conditions, cause the laser 105 to alternately begin and cease lasing sufficiently often that the laser 105 either does not remain in a lasing state long enough to exhibit a dominant lasing mode or, if it does, does not remain in a lasing state long enough for that dominant lasing mode to hop to a new mode.

Finally with respect to the signal generator 125, it should be noted that, although the drive signal is a current signal in the embodiment depicted in FIG. 1, the drive signal can generally be of any form that would induce a particular laser to produce a laser beam. The particular form of the drive signal depends upon the particular laser being utilized.

Figure 2:
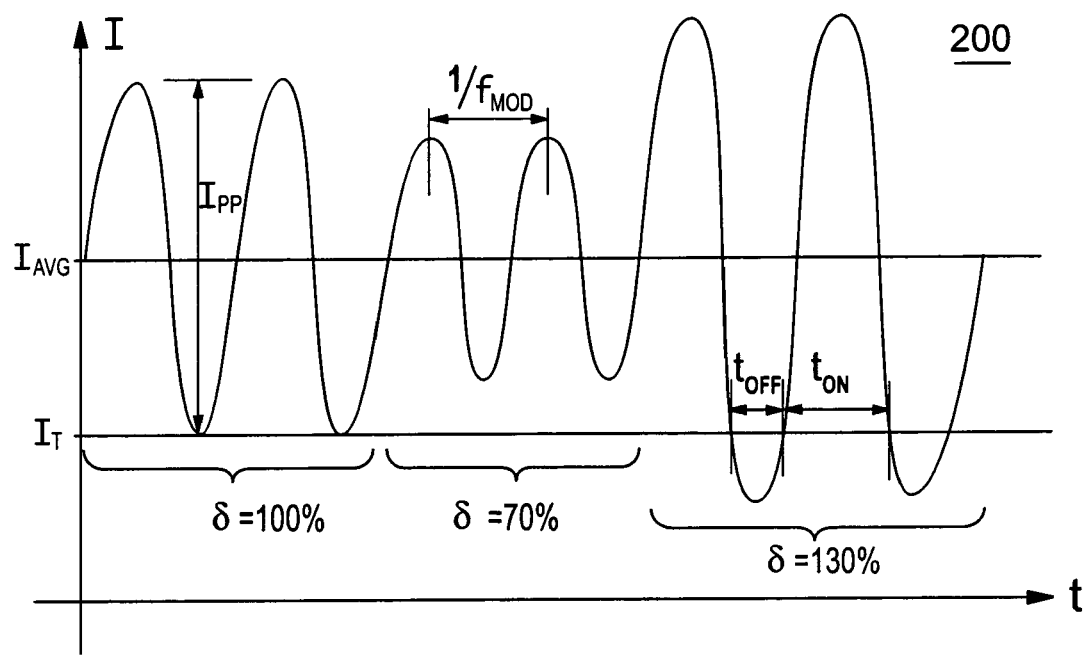
FIG. 2 is a time-domain plot of a laser drive current utilized in the system of FIG. 1.

FIG. 2 is a time-domain plot 200 of an exemplary form of the laser drive current I utilized in the system 100. The plot 200 depicts the amplitude of the drive current I as a function of time. To illustrate the pertinent principles, three periodic sinusoidal waveform segments are shown, with three different peak-to-peak amplitudes ($I_{pp}$) in three different regions. In all regions, the frequency of the waveform is $f_{MOD}$, and the drive current I has an average value $I_{AVG}$. Also illustrated in the plot 200 is $I_T$, the lasing threshold of the laser 105. When the drive current I exceeds the threshold $I_T$, the laser 105 is in a lasing state, i.e., the laser 105 is "on"; when $I<I_T$, the laser 105 is "off" or not in a lasing state.

The three regions of the plot 200 illustrate three different values of the modulation depth $\delta$. In the first region (shown on the left), the modulation depth $\delta$ is 100%, meaning that the amplitude of the drive current I at its waveform trough approximately equals the laser threshold. In mathematical terms, $\delta \approx 100\%$ corresponds to the case in which $I_{pp} \approx 2(I_{AVG}-I_T)$. The second (middle) region illustrates an under-modulated case, in which $\delta \approx 70\%$, corresponding to $I_{pp} \approx 2 \cdot 70\% (I_{AVG}-I_T)$. Finally, in the third (right) region, the drive current I is over-modulated; in particular, $\delta \approx 130\%$ and $I_{pp} \approx 2 \cdot 130\% (I_{AVG}-I_T)$. The system 100 preferably operates in the over-modulated case (i.e., in which $\delta > 100\%$). In that case, the laser 105 is alternately on and off. As illustrated in the plot 200, the duration of the on state is denoted $T_{ON}$, while the duration of the off state is denoted $T_{OFF}$. Preferably, $f_{MOD}$ is chosen such that $T_{ON}$ is sufficiently small that the laser 105 cannot appreciably hop from one dominant mode to another during that time. As one example with one particular laser, $f_{MOD}$ at or above approximately 350 MHz (megahertz) has been found to work satisfactorily with an SDL 5401 laser. While it is preferred that the system 100 operates such that $\delta > 100\%$, it may be possible in some cases to achieve the same effect when the modulation depth $\delta$ is approximately equal, or even slightly less than, 100%, as the threshold $I_T$ is typically an approximation.

Figure 3B:
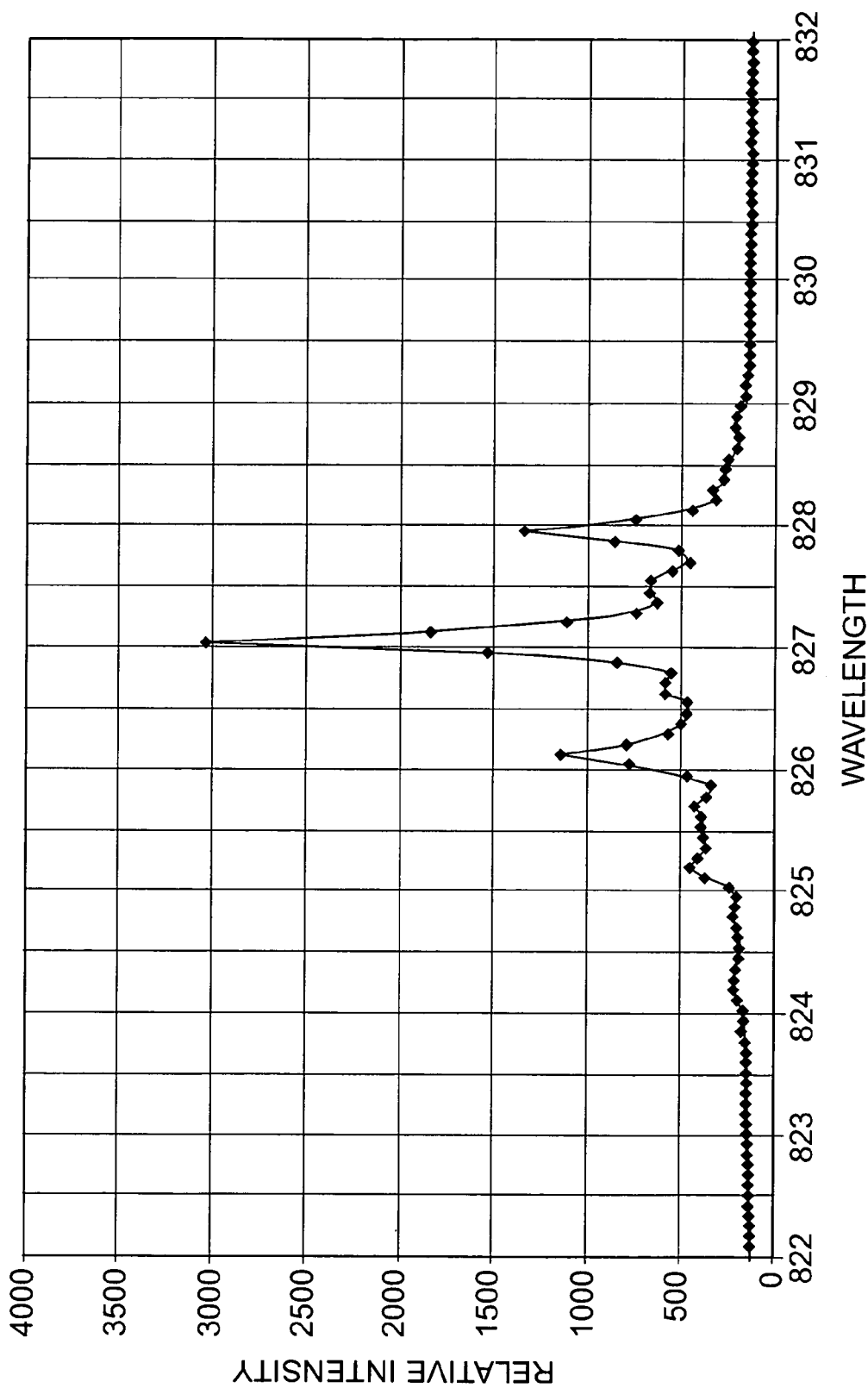

FIGS. 3A and 3B are wavelength-domain plots of the spectrum of the laser beam 130. FIG. 3A shows the laser's spectrum without modulation, while FIG. 3B shows the laser's spectrum with modulation as provided by the system 100. In both plots, the horizontal axis represents laser wavelength in nanometers, and the vertical axis represents relative intensity of the laser beam. As can be seen in FIG. 3A, the spectrum of an unmodulated laser beam exhibits a single dominant mode at approximately 825.28 nm (nanometers). The spectrum of a modulated laser beam, as shown in FIG. 3B, however, exhibits multiple modes. The data shown in FIG. 3B was taken by measurements of an SDL 5401 laser modulated with a 320 MHz sinusoidal signal at a modulation depth of approximately 105%. Modes are discernable at approximately 826.12 nm, 827.04 nm, and 827.96 nm. Other modes might also be present but not detectable with the limited resolution of the spectrum analyzer utilized to collect the data shown in FIG. 3B. The exact number and spacing between the various modes are not critical.

Figure 4:
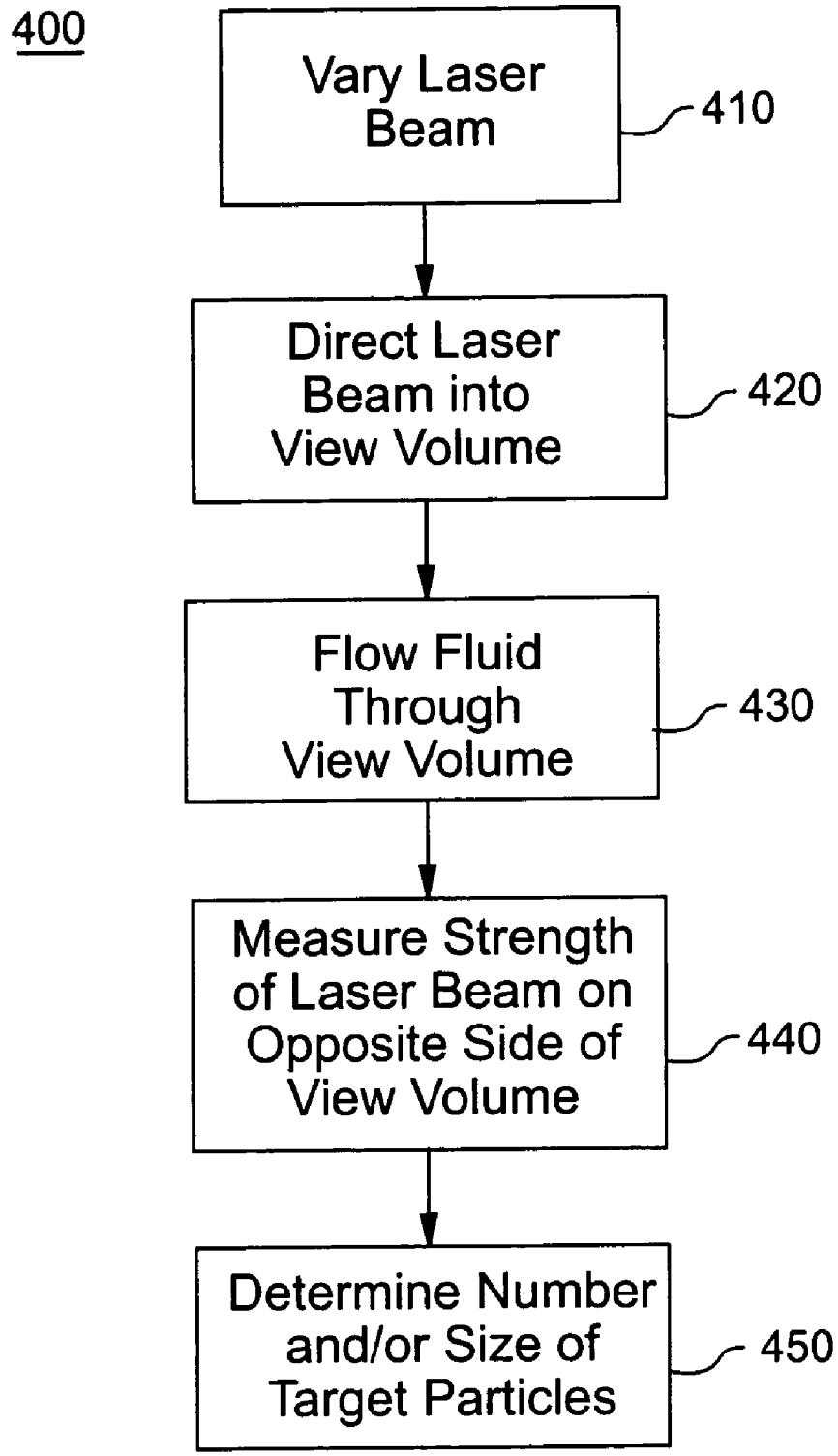
FIG. 4 is a flowchart of a method, according to one embodiment.

FIG. 4 is a flowchart of a method 400, according to one embodiment. The method 400 varies (410) a laser beam. The varying step 410 may comprise spreading the spectrum of the laser beam; causing the laser beam to exhibit multiple, effectively simultaneous lasing modes; or rapidly turning the laser beam alternately on and off. The method 400 also directs (420) the laser beam into a view volume. The directing step 420 optionally involves focusing the laser beam to have a desired footprint on the view volume and/or a detector behind the view volume. The method 400 also flows (430) a carrier fluid through the view volume. The flowing step 430 is optional, as the fluid under test may be a still sample. Next, the method 400 measures (440) the strength of the laser beam exiting the view volume on its opposite side. Finally, the method 400 determines (450) a number and/or size of target particles in the view volume, based on the results of the measuring step 440. While the steps of the method 400 are illustrated in a particular order, that particular order need not be imposed. Those skilled in the art will readily appreciate, that steps can be performed in different orders or simultaneously.

The terms and descriptions used herein are set forth by way of illustration only and are not meant as limitations. Those skilled in the art will recognize that many variations can be made to the details of the above-described embodiments without departing from the underlying principles of the invention. The scope of the present invention should, therefore, be determined only by the following claims, and their equivalents, in which all terms are to be understood in their broadest reasonable sense unless otherwise indicated.

The invention claimed is:

1. In an optical particle detection system of a light-extinction type that includes a view volume through which a laser beam propagates and a stream of target particles immersed in a carrier fluid flows, the laser beam striking the target particles and thereby affecting an amount of the laser beam that is incident on a light-sensitive detector positioned in optical communication with the view volume, the light-sensitive detector producing in response to the incident laser beam a detection signal corresponding to a number and/or size of target particles in the stream, the laser beam propagating from a laser source in response to a drive current amplitude that reaches a lasing threshold and characterized by noise energy that is produced by spurious switching of laser operating modes, a method of controlling the laser source to emit a laser beam in which the noise energy is suppressed to a level that does not appreciably affect the fidelity of the signal produced by the light-sensitive detector, the method comprising:

modulating the drive current amplitude to transition across the lasing threshold by a selected amount and at a selected frequency to purposefully cause multiple simultaneous laser operating modes, the selected amount and frequency of modulation of the drive current amplitude cooperating to cause the spurious mode switching to occur among a number of laser operating modes sufficient to spread the noise energy produced over a spectral range established by the number of laser operating modes, the spreading of the noise energy causing the noise energy to maintain a level to which the light-sensitive detector does not appreciably respond in the production of the detection signal.

2. The method of claim 1, wherein the light-sensitive detector is characterized by a maximum response frequency, and wherein the controlled frequency of modulation is substantially greater than the maximum response frequency.

3. The method of claim 1, wherein the laser source includes a diode laser.

4. The method of claim 3, wherein the diode laser is of an index-guided type.

5. The method of claim 1, wherein the selected frequency of modulation operates at about a 50% duty cycle and the selected amount of drive current modulation represents a depth of modulation of at least about 100%.

6. The method of claim 1, wherein the selected frequency of modulation is about 350 MHz.

7. The method of claim 1, wherein the laser beam propagates along a propagation path and the optical particle detector system further comprises an optical element positioned along the laser beam propagation path, the optical element being tilted at an angle by an amount relative to the propagation path to direct back reflections of light incident on the optical element away from the laser source and thereby prevent an addition of back reflection light energy that induces additional noise.

8. The method of claim 1, wherein the fluid is a liquid.

9. A light extinction-type optical particle detection system, comprising:

a laser source that produces a laser beam, the laser beam propagating from the laser source in response to a drive current having an amplitude that reaches a lasing threshold, the laser beam characterized by mode-hopping noise energy that is produced by spurious switching of laser operating modes;

a view volume through which the laser beam propagates and a stream of target particles immersed in a carrier fluid flows;

a light-extinction type detector positioned on a side of the view volume opposite of the laser course, the laser beam striking the target particles and thereby affecting an amount of the laser beam that is incident on the detector, the detector producing in response to the incident laser beam a detection signal corresponding to a number and/or size of target particles in the view volume; and a signal generator that produces the drive current such that the drive current amplitude transitions across the lasing threshold by a selected amount and at a selected frequency to purposefully cause the laser beam to operate simultaneously in multiple lasing modes, the selected amount and frequency cooperating to spread the mode-hopping noise energy over a spectral range established by the number of simultaneously operating lasing modes, such that the detector does not appreciably respond to the mode-hopping noise energy when producing the detection signal.

10. The system of claim 9, wherein the light-extinction type detector is characterized by a maximum response frequency, and in which the selected frequency is substantially greater than the maximum detector response frequency.

11. The system of claim 10 further comprising:

electronic circuitry connected to the light-extinction type detector, wherein the electronic circuitry produces the detection signal in response to the laser beam incident upon the detector, and wherein the maximum response frequency is based in part upon the characteristics of the electronic circuitry.

12. The system of claim 9, wherein the laser source includes a diode laser.

13. The system of claim 12, wherein the diode laser is of an index-guided type.

14. The system of claim 9, wherein the selected frequency operates at about a 50% duty cycle and the selected amount represents a depth of modulation of the laser source exceeding about 100%.

15. The system of claim 9, wherein the selected frequency is about 350 MHz.

16. The system of claim 9, wherein the laser beam propagates along a propagation path and the optical particle detection system further comprises:

an optical component positioned along the laser beam propagation path, the optical component being tilted at an angle by an amount relative to the propagation path to direct back reflections of light incident on the optical component away from the laser source and thereby prevent an addition of back reflection light that induces additional noise energy.

17. The system of claim 9, wherein the fluid is a liquid.

18. An apparatus comprising:

a view volume through which a laser beam propagates and a stream of target particles immersed in a carrier fluid flows;

means for detecting light, positioned in optical communication with the view volume;

means for generating a laser beam striking the target particles and thereby affecting an amount of the laser beam that is incident on the means for detecting light, the laser beam being characterized by noise energy that is produced by spurious switching of laser operating modes;

means for producing, in response to the incident laser beam, a detection signal corresponding to a number of target particles in the stream; and means for spreading the noise energy over a spectral range, whereby the noise energy is maintained at a level to which the means for producing does not appreciably respond in the production of the detection signal.

19. The apparatus of claim 18, wherein the means for detecting light is an extinction-type detector.

20. The apparatus of claim 18, wherein the means for generating a laser beam includes a diode laser.

21. The apparatus of claim 20, wherein the diode laser is of an index-guided type.

22. The apparatus of claim 18, wherein the fluid is a liquid.

23. The apparatus of claim 18, wherein the means for generating a laser beam generates the laser beam in response to a drive signal, and in which the means for spreading comprises a means for varying the drive signal.

24. The apparatus of claim 18, wherein the means for spreading comprises a means for rapidly turning the means for generating a laser beam alternately on and off.

25. The apparatus of claim 18, wherein the means for spreading comprises a means for modulating the laser beam.

26. The apparatus of claim 18, wherein the means for spreading comprises a means for causing the laser beam to operate in multiple lasing modes simultaneously.

* * * * *